United States Patent [19]

Saunders

[11] 4,245,512
[45] Jan. 20, 1981

[54] FABRIC STRETCH TESTING DEVICE

[75] Inventor: Eugene M. Saunders, Concord, Calif.

[73] Assignee: Levi Strauss & Co., San Francisco, Calif.

[21] Appl. No.: 49,153

[22] Filed: Jun. 18, 1979

[51] Int. Cl.³ ............................................. G01N 3/08
[52] U.S. Cl. ................................... 73/789; 73/828
[58] Field of Search ...................... 73/789, 828, 159

[56] References Cited

U.S. PATENT DOCUMENTS

| 169,376 | 11/1875 | Scott | 73/789 |
|---|---|---|---|
| 1,817,617 | 8/1931 | Gosch | |
| 2,187,914 | 1/1940 | Reitan | |
| 2,563,881 | 8/1951 | Steadman | 73/828 |
| 3,316,757 | 5/1967 | Fletcher et al. | |
| 3,400,576 | 9/1968 | Siciliano | |
| 3,444,728 | 5/1969 | Burns | |

Primary Examiner—S. Clement Swisher
Attorney, Agent, or Firm—Limbach, Limbach & Sutton

[57] ABSTRACT

A fabric sample is stretched between two grippers mounted on two moveable parts, one of which slides on the other. A pair of plier-like hand grips exerts a force through a coil spring on the two moveable parts so that the displacement of the two parts relative to each other measures the amount of stretch of the fabric sample whereas the amount of compression of the spring indicates the force being applied to achieve that amount of stretching.

7 Claims, 4 Drawing Figures

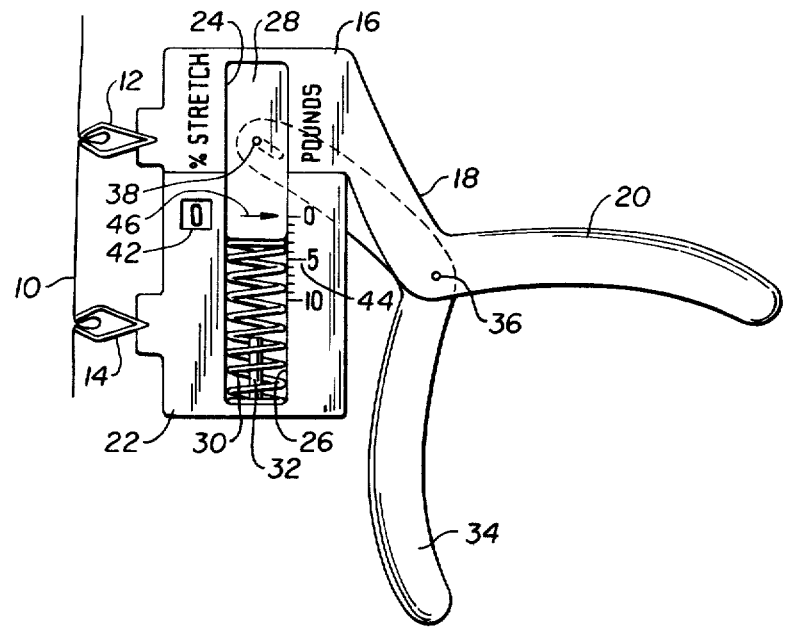
FIG._1.
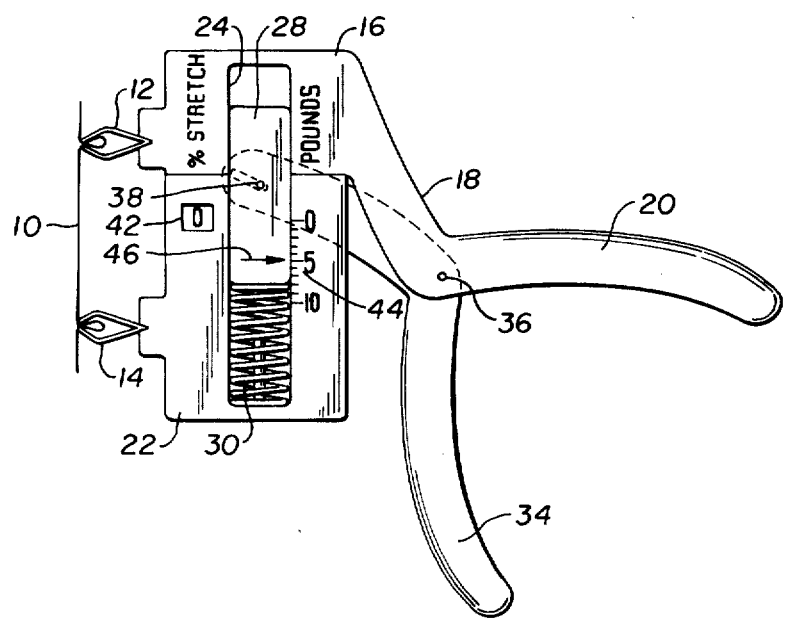
FIG._2.

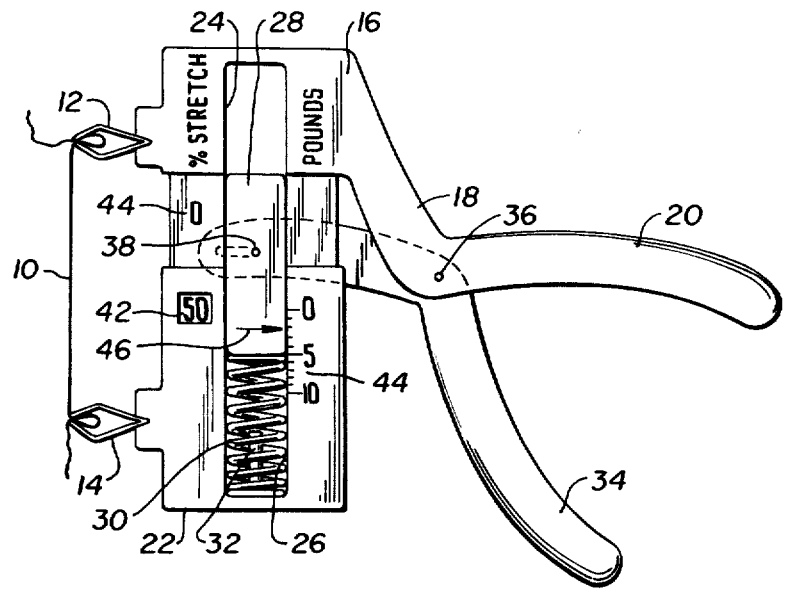
FIG._3.
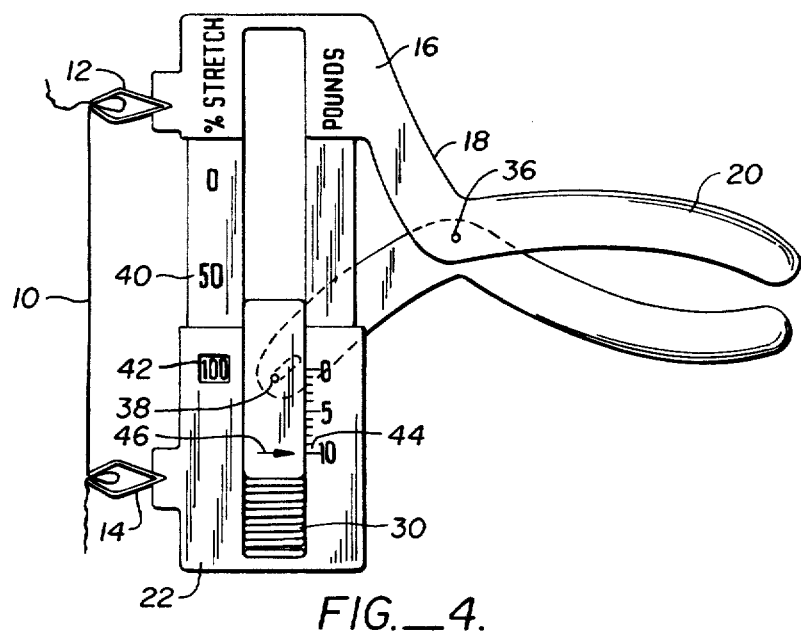
FIG._4.

FABRIC STRETCH TESTING DEVICE

BACKGROUND OF THE INVENTION

This invention relates to apparatus for testing the stretch of a sample of fabric, and more particularly to a hand-held stretching device.

The amount of stretch of the fabric is an important consideration in manufacturing garments. The need for a particular amount of stretch requires basic consideration in the early development stages, such as when choosing the fiber or yarn type. There are a number of different methods for measuring stretch, such as applying a known force to put the fabric in tension, as with a standard weight, and then measuring the percent increase in length of the fabric.

By far the most often used test, however, is the "hand stretch" method, whereby the fabric is simply pinched between the fingers and pulled until near maximum stretch is reached. If accuracy is required, a ruler is used to measure the increased length. The major drawback, of course, to this method is the poor correlation to the objective laboratory methods, or even to different persons making the tests. The great advantages of this method are that it is convenient, inexpensive, quick and portable. Thus, what is desired is a device which will elongate a given fabric sample to determine its stretch propensity, quantify this stretch at a pre-determined load, and retain the fabric in a stretched state for a specified period of time, whereupon relaxation the percent unrecovered stretch can be measured.

SUMMARY OF THE INVENTION

The foregoing and other objectives are achieved by means of the fabric stretching device according to the invention which comprises a first member and a second member slideable on the first member with each of the members having a single gripper mounted thereon for stretching a fabric sample therebetween, and a third member which slides relative to the first and second members and which compresses or stretches a spring connected between it and the second member so that force supplied to compress or stretch the spring causes relative movement between the first and second members. By noting the amount of compression or tension in the spring depending on the type of spring used, the amount of force being applied to the fabric sample can be quantified. The amount of relative movement between the first and second members indicates the amount of stretch of the fabric sample.

In the preferred embodiment of the invention, the force is applied to the spring by means of a pair of plier-like handles, one of which is firmly attached to the first member and the second of which is pivoted at its midpoint to an extension of the first member and at one end to the third member. Indicating means are marked on the first and second members to show the relative movement between them, and also on the second and third members to show the amount of movement of the spring. In the preferred embodiment the spring is of the compression type.

It is therefore an object of the invention to provide a portable fabric stretcher tester.

It is another object of the invention to provide an easily operated fabric stretcher tester.

It is still another object of the invention to provide an inexpensive fabric stretch tester.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWINGS

FIGS. 1-4 are vertical, elevational views, shown in a stretching sequence, of the fabric stretching device according to the invention.

DETAILED DESCRIPTION OF THE PREFERRED EMBODIMENT

Referring now more particularly to FIG. 1 a fabric sample 10 (shown in the figures diagramatically) is held taut between a first gripper 12 and a second gripper 14. These grippers are resilient and hand-operated. The gripper 12 is mounted on a first member 16 which has a projecting portion 18 from which a handle 20 extends more or less at a 90°-100° angle.

A second member 22 is mounted slideably on the member 16, as perhaps can best be viewed in FIGS. 3 and 4. The member 22 has projecting edges (not shown) which slide in appropriate grooves or slots (not shown) of the member 16 so that the member 22 is confined to relative movement in a direction which is vertical, as viewed in the figures.

The member 16 is provided with a slot 24 which extends in a line just parallel to the taut fabric sample held between the grippers 12 and 14. Similarly the member 22 has a corresponding slot 26 which is co-extensive with at least a portion of the slot 24 at the point where the member 22 overlaps the member 16. A rectangularly shaped member 28 is slideably mounted within the slots 24 and 26 so that it can move in the direction of the length of the slot. A coil spring 30 is mounted at a closed end of the slot 26 and held in place by a pin 32 projecting from the interior surface of the slot 26 of the member 22. Member 28 bears against the other end of the spring so that longitudinal movement of the member 28 in the slots 24 and 26 serves to press the spring 30 against the closed end of the slot 26 and thus to move the member 22 with respect to the member 16.

The member 28 is moved in the slots 24 and 26 by means of a second handle 34 which is pivotally attached at its midpoint 36 to the extension 18 of the member 16 at the point where the handle 20 attaches to the extension 18. One end of the handle 34 is pivotally attached to the member 28 by a pin in groove mounting 38. It will be appreciated that when the free end of the handle 34 is squeezed toward the free end of the handle 20 the end of the handle 34 which is attached to the member 28 will be caused to move the member 28 downwardly as viewed in the figures. The figures sequentially show such motion taking place. As the member 28 moves downwardly, the fabric sample between the grippers 12 and 14 will restrain the movement of the member 22 relative to the member 16. As more force is applied through the member 28 and the spring 30 to the member 32 the spring 30 will be compressed. Because the amount of compression of the spring is directly proportional to the applied force a measurement of the spring's compression will give an indication of the tension force being applied to a fabric sample between the grippers 12 and 14. Also because the relative movement between the members 16 and 22 is only possible due to stretch in the fabric sample between the grippers 12 and 14, the amount of relative movement is an indicator of the amount of stretch in the fabric.

In order to measure these two factors, a scale 40 is marked on the number 16 at the point where it is overlapped by the member 22. The member 22 is provided with a window 42 through which the indicia of the scale 40 can be viewed. Thus as the member 22 moves relative to the member 16 different indicia on the scale 40 are viewed through the window 42 thereby indicating the relative movement between the two members.

In order to show the amount of compression of the spring 30 a scale 44 is marked on the member 22 and an indicating line 46 is correspondingly marked on the member 28. The displacement of the indicating line 46 relative to the scale 44 shows the amount of movement of the member 28 with respect to the member 22 and, hence, the amount of compression of the spring 30. As indicated above, the amount of compression of the spring 30 is a direct measure of the tension force applied to the sample 10 stretched taut between the grippers 12 and 14.

It will be appreciated that many modifications of the above described embodiment are possible without departing from the spirit and scope of the invention. For example, the member 28 could be moved relative to the members 16 and 22 by means of a threaded shaft which is threadably engaged in the member 16, so as to extend in the direction of the slot 24. By turning the shaft, the member 28 would be moved down the length of the slot 24. Also, in a far less advantageous embodiment than the preferred embodiment, a tension spring could be attached between one end of the handle 34 and the member 22. The rather obvious difficulties with this form of the embodiment are that it is less compact and is more difficult to arrange the various scales showing the various amount of stretch and the stretching force.

The terms and expressions which have been employed here are used as terms of description and not of limitations, and there is no intention, in the use of such terms and expressions of excluding equivalents of the features shown and described, or portions thereof, it being recognized that various modifications are possible within the scope of the invention claimed.

What is claimed is:

1. A device for testing the stretchability of a fabric sample comprising
    a first member,
        a first gripper mounted on the first member for engaging the sample,
    a second member, slideably mounted on the first member,
    a second, sample gripper mounted on the second member for engaging the sample,
    a third member,
    a spring connected between the second and third members and,
    means for applying a separating force between the first and third members which force is transmitted through the spring to the second member to cause it to slide relative to the first member and thereby increase the spacing between the first and second grippers, the force applying means being pivoted on the first member, whereby the fabric sample between the first and second grippers is placed in tension.

2. A stretchability testing device as recited in claim 1 wherein the third member is slideably mounted on the first member.

3. A stretchability testing device as recited in claim 1 or 2 further comprising indicia on one of the first and second members for displaying the degree of movement of one with respect to the other as an indication of the amount of the stretch of the sample when subjected to tension by the testing device.

4. A stretchability testing device as recited in claim 1 or 2 further comprising indicia on one of the second and third members for displaying the degree of movement of one with respect to the other as an indication of the amount of force applied to the spring, and hence, the tension force applied to the sample between the first and second grippers.

5. A stretchability testing device as recited in claim 2 wherein the spring is a compression spring mounted between the second and third members.

6. A device for testing the stretchability of a sample of stretchable material comprising
    a first member having a slotted portion therein,
    a first gripper for engaging the sample and mounted on the first member,
    a second member slideably mounted on the first member and having a recess therein,
    a second gripper for engaging the sample and mounted on the second member
    a compression spring carried in the recess in the second member and bearing against it at one end,
    a third member slideably mounted in the slot in the first member and bearing against the other end of the compression spring,
    a first handle attached to the first member,
    a two ended, second handle which is pivotally attached at one end to the third member and is pivotally attached to the first member at a point intermediate the ends of the second handle,
    a first scale marked on one of the first and the second members and a first indicator, co-operating with the first scale, mounted on the other of the first and second members, the first scale and the first indicator together displaying the degree of relative movement between the first and second grippers and hence, the amount of stretch of the sample, and
    a second scale marked on one of the second and the third members for displaying the degree of movement of one with respect to the other as an indication of the amount of force applied to the spring and hence, the tension force applied to the sample between the first and second grippers.

7. A device for testing the stretchability of a fabric sample comprising
    a first member,
        a first gripper mounted on the first member for engaging the sample,
    a first handle mounted on the first member,
    a second member, slideably mounted on the first member,
    a second, sample gripper mounted on the second member for engaging the sample,
    a third member,
    a spring connected between the second and third members and,
    means for applying a separating force between the first and third members which force is transmitted through the spring to the second member to cause it to slide relative to the first member and thereby increase the spacing between the first and second grippers, the force applying means including a two-ended second handle pivoted at one end to the third member and at a point intermediate its ends to the first member whereby when the first and second handles are squeezed together, a separating force is applied between the first and third members, and the fabric sample between the first and second grippers is placed in tension.

* * * * *